(12) United States Patent
Huffman et al.

(10) Patent No.: US 7,848,478 B1
(45) Date of Patent: Dec. 7, 2010

(54) SYSTEM FOR OPTICAL COMMUNICATION BETWEEN STATIONARY AND NON-STATIONARY PARTS AND METHOD OF MAKING SAME

(75) Inventors: Nathanael D. Huffman, Sussex, WI (US); Phil E. Pearson, Hartland, WI (US); James Charles Bartelsen, Nashotah, WI (US)

(73) Assignee: General Electric Company, Schenectady, NY (US)

( * ) Notice: Subject to any disclaimer, the term of this patent is extended or adjusted under 35 U.S.C. 154(b) by 730 days.

(21) Appl. No.: 11/744,343

(22) Filed: May 4, 2007

(51) Int. Cl.
*A61B 6/00* (2006.01)

(52) U.S. Cl. ............................... 378/4; 378/15

(58) Field of Classification Search ............... 378/4, 378/15, 19; 250/551, 217, 208.1
See application file for complete search history.

(56) References Cited

U.S. PATENT DOCUMENTS

| 6,104,849 | A  | * | 8/2000  | Lewis et al. | 385/26 |
| 6,816,566 | B2 | * | 11/2004 | Hamada et al. | 378/15 |

* cited by examiner

*Primary Examiner*—Irakli Kiknadze
(74) *Attorney, Agent, or Firm*—Ziolkowski Patent Solutions Group, SC

(57) ABSTRACT

An optical communication system includes a rotatable base having a plurality of optical sources and optical receivers mounted thereon, and a stationary base having a plurality of optical sources and optical receivers mounted thereon. The system is configured to send and receive optical signals bi-directionally between the rotatable base and the stationary base while the rotatable base is rotating.

24 Claims, 7 Drawing Sheets

SYSTEM FOR OPTICAL COMMUNICATION BETWEEN STATIONARY AND NON-STATIONARY PARTS AND METHOD OF MAKING SAME

BACKGROUND OF THE INVENTION

The present invention relates generally to diagnostic imaging and, more particularly, to an apparatus and method of manufacturing an optical communication between a rotatable base and a stationary base of a CT gantry.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

A CT system typically includes a gantry to provide mechanical support and functionality to the CT system. The gantry typically includes a stationary mechanical base, a rotatable mechanical base, electronics (circuit boards, cable assemblies, and power supplies) mounted on the stationary mechanical base, electronics (circuit boards, cable assemblies, power supplies), and an x-ray source. Generally, the x-ray source and the detector array are mounted to the rotatable base and rotated about an imaging volume and about the subject. The x-ray source typically includes an x-ray tube, which emits an x-ray beam at a focal point.

The detector array typically includes a collimator for collimating x-ray beams received at the detector, a scintillator for converting x-rays to light energy adjacent the collimator, and a photodiode array for receiving the light energy from the adjacent scintillator and producing electrical signals therefrom. Typically, the scintillators are arranged in a scintillator array to convert x-rays to light energy. Each scintillator discharges light energy to a photodiode adjacent thereto. Each photodiode detects the light energy and generates a corresponding analog electrical signal which is then digitized and transmitted to the data processing system for image reconstruction.

Because the detector array is rotated with the rotatable base, digitized electrical signals generated therein may be transmitted from the rotatable base to the stationary base, where data processing and image reconstruction may take place. Such data is typically transmitted over a high-speed, capacitively coupled, unidirectional line. Additionally, software data and hardware commands are typically transmitted between the stationary base and the rotating base in order to control aspects of the system operations on the rotating base. Data is also often typically transmitted between the rotating side and the stationary side to provide, for instance, system status.

A brush-based system is typically used for carrying software generated TCP/IP data and hardware commands related to operation of the imaging system. Such systems are typically referred to as low-speed communication lines. Data transmitted on low-speed communication lines is typically binned in two ways:

1. Software generated TCP/IP data typically contains information needed by circuit boards on the rotating base of the gantry in order for the circuit boards to function correctly. Such information may include, for example, scan setup parameters, error log feedback, and status. The software data is typically transmitted bi-directionally. Thus, in a brush-based system, each direction of data transmission (i.e., to/from the rotating side) may use one sliding contact ring.

2. Hardware generated commands related to operation of the system is also typically transmitted via the brush-based system. Such information may include, for example, commands directing the system to turn on/off x-rays, and realtime encoder feedback from the stationary axial encoder to the DAS as trigger commands. The hardware generated commands are typically uni-directional and transmitted to the rotating base. The hardware commands are typically shared with the low-speed communication line that transmits the software generated TCP/IP data to the rotating base.

However, in recent years, gantry run speeds have been increasing. Because brush-based data transmission systems are wear items, communication between the stationary and rotating sides tends to degrade as the brushes wear, and the wear-rate increases with an increased gantry run speed. Brush-based systems also require periodic maintenance, such as cleaning and replacement of wear items, which adds overall cost to the system, the cost of which increases with gantry run speed. Furthermore, brush-to-ring tolerance requirements increase because faster gantry run speeds are more sensitive to brush-ring misalignment. Additionally, the ring in a brush-based system can serve as an antenna which can be a noise source that interferes with signals and data transmitting therethrough.

Finally, as gantry run speeds increase, so too does the required rate of hardware generated command transmission in the form of DAS trigger commands. Data transmission rates are regulated and limited, however, because of the emissions that radiate therefrom. Meeting regulated emission requirements is therefore increasingly difficult with increased gantry run speed.

Therefore, it would be desirable to design an apparatus and method of manufacturing a gantry communication system with greater communication bandwidth, increased noise immunity, brushless operation, and a modular design to provide bi-directional communications for software data and hardware commands between the rotating and stationary bases of a CT gantry.

BRIEF DESCRIPTION OF THE INVENTION

The present invention is a directed method and apparatus for a gantry communication system with greater communication bandwidth, increased noise immunity, brushless operation, and an inexpensive design to provide bi-directional communications for software data and hardware commands between the rotating and stationary bases of a CT gantry.

According to one aspect of the present invention, an optical communication system includes a rotatable base having a plurality of optical sources and optical receivers mounted thereon, and a stationary base having a plurality of optical sources and optical receivers mounted thereon. The system is configured to send and receive optical signals bi-directionally between the rotatable base and the stationary base.

In accordance with another aspect of the invention, a method of manufacturing a communication system between a rotating base and a stationary base includes attaching a first printed wire assembly (PWA) to a rotatable base, the first PWA having mounted thereon at least one light source and at least one light receiver, attaching a second PWA to a stationary base, the second PWA having mounted thereon at least one light source and at least one light receiver. The method further includes positioning the rotatable base and the stationary base proximate to one another, emitting light from one of the first and second PWAs, and receiving the light by the other of the first and second PWAs.

Yet another aspect of the present invention includes a CT system having a high frequency electromagnetic energy projection source configured to project a high frequency electromagnetic energy beam toward an object, a detector array having a plurality of scintillator cells wherein each cell is configured to detect high frequency electromagnetic energy passing through the object, and a data acquisition system (DAS) connected to the detector array and configured to receive outputs from detector array. The CT system further includes a rotatable gantry having an opening to receive the object to be scanned, the rotatable gantry having a rotatable base and a stationary base positioned proximate the rotatable base, a plurality of modules each having at least one light source and at least one light receiver positioned thereon, wherein at least one of the plurality of modules is mounted on the rotatable base, and wherein at least one of the plurality of modules is mounted on the stationary base, and a computer programmed to send and receive optical signals bi-directionally between the rotatable base and the stationary base while the rotatable base is rotating and while the rotatable base is stationary.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a sixty-four-slice computed tomography (CT) system. However, it will be appreciated by those skilled in the art that the present invention is equally applicable for use with systems in general that require digitized signals to be passed from a stationary component to a non-stationary component. Furthermore, one skilled in the art would recognize that the present invention is equally applicable to other multi-slice CT configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
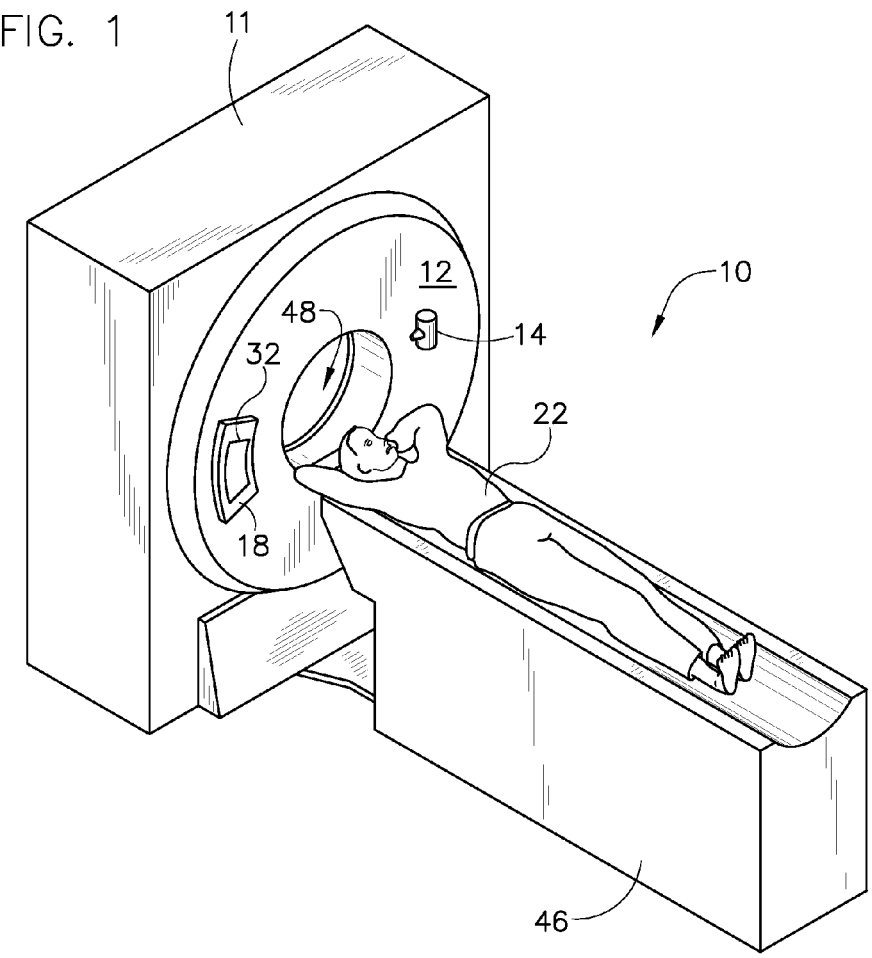
FIG. 1 is a pictorial view of a CT imaging system.
Figure 2:
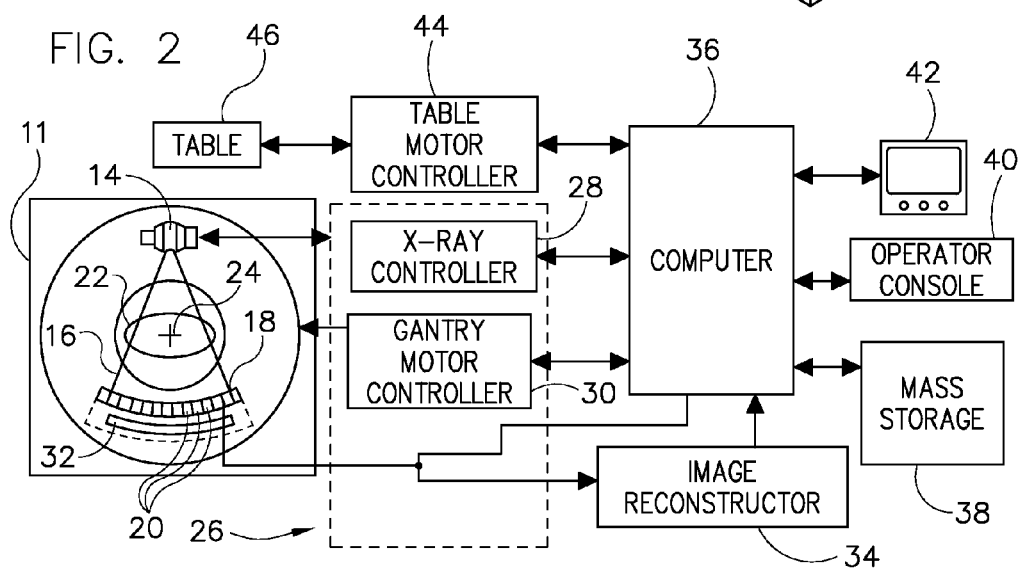
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has a cover 11 thereon which is typically attached to gantry 12 for aesthetic reasons. Beneath cover 11, gantry 12 has an x-ray source 14 that projects a beam of x-rays 16 toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 on FIG. 1 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 relative to gantry 12. Particularly, table 46 moves patient 22 through a gantry opening 48 of FIG. 1 in whole or in part.

Figure 3:
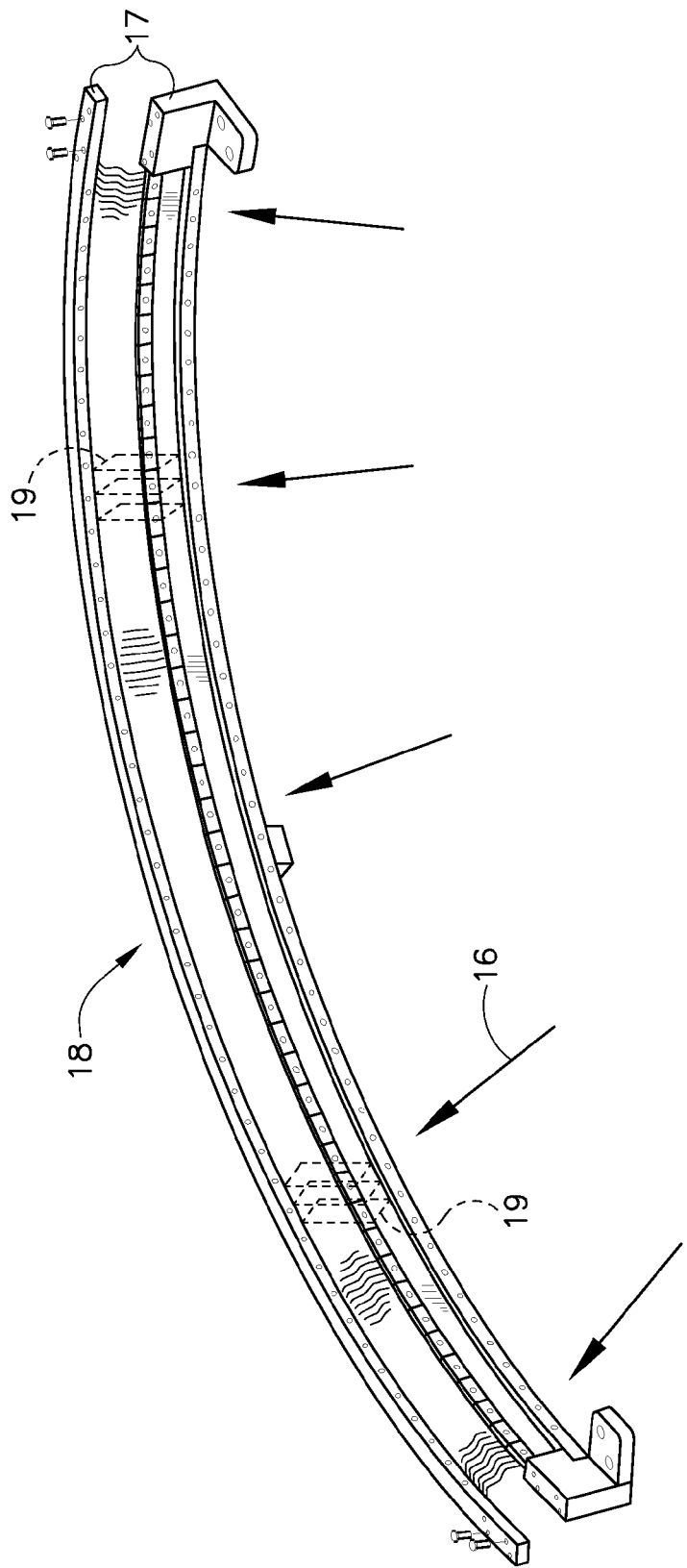
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
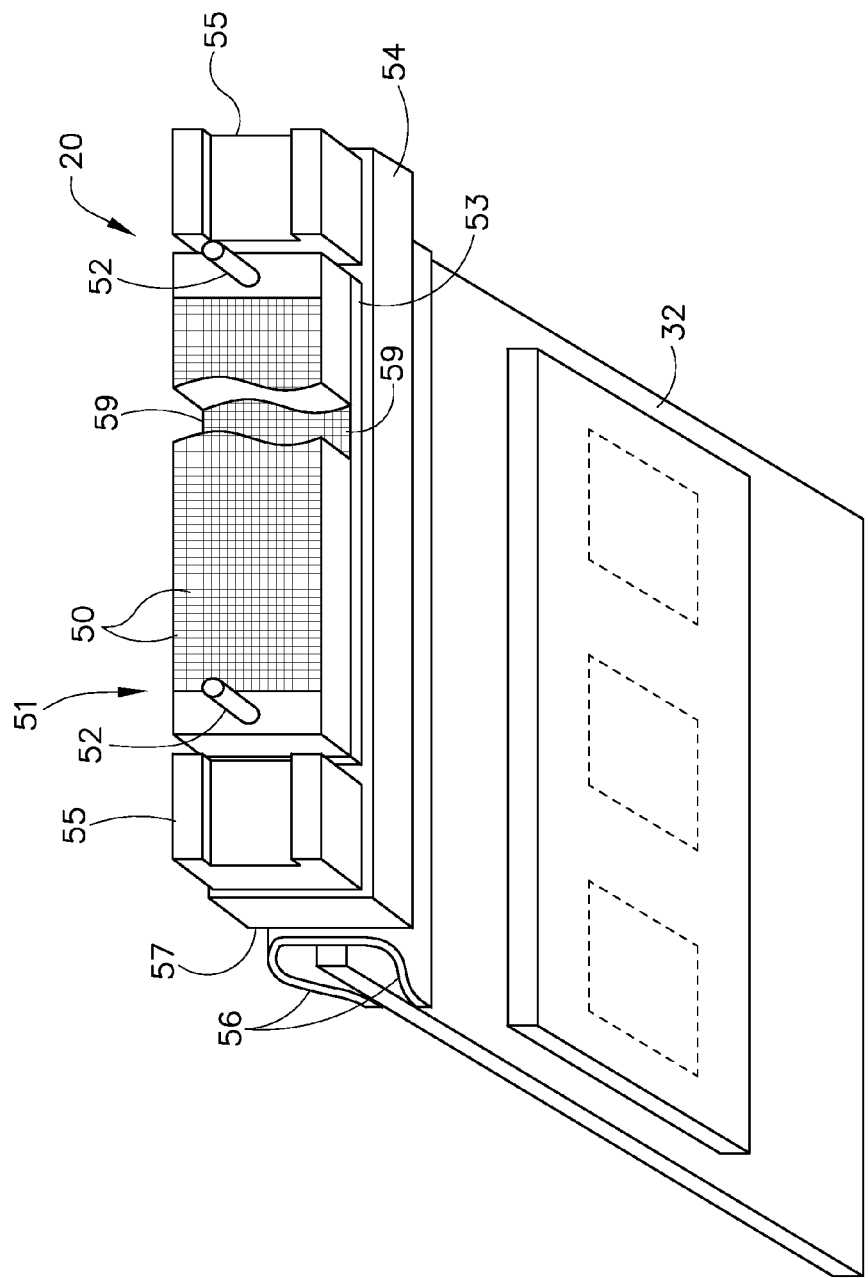
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal, which is typically transmitted as a high-speed digital signal across the capacitively coupled contactless link.

Figure 5:
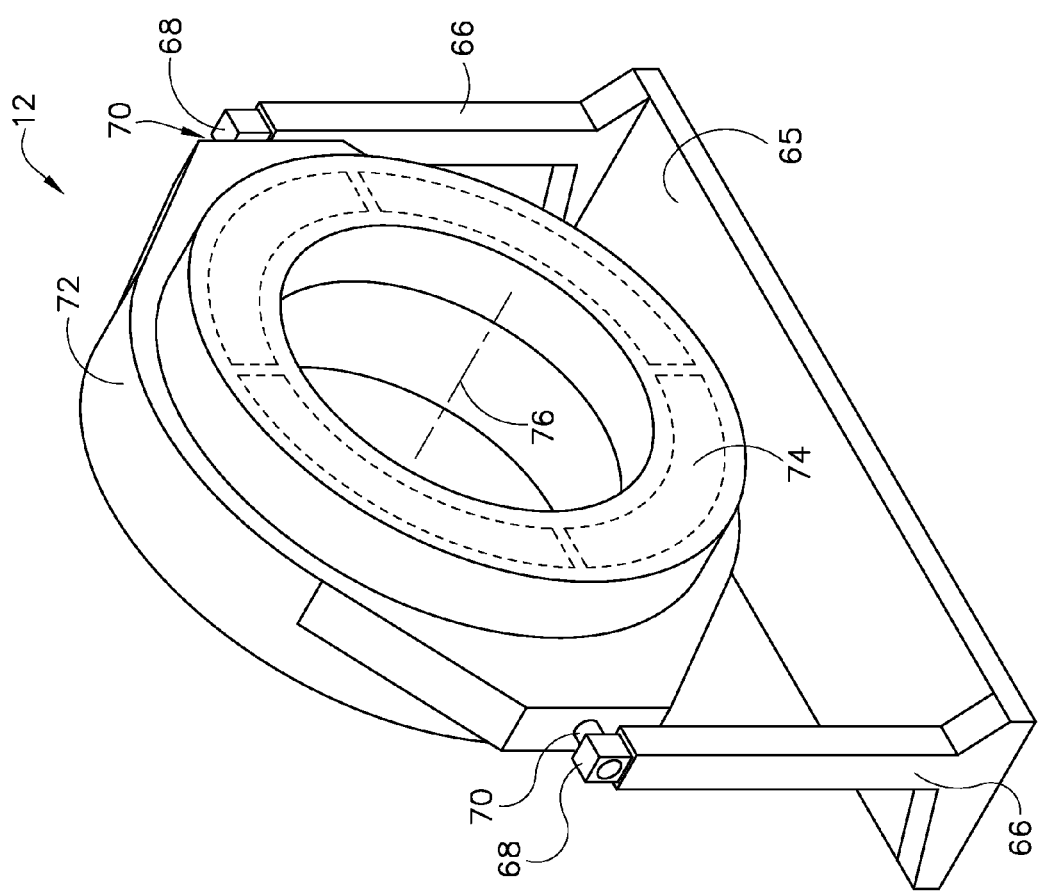
FIG. 5 is a perspective view of a CT gantry.

Referring now to FIG. 5, gantry 12, illustrated without cover 11 of FIGS. 1 and 2, typically includes a stationary base 65 having support arms 66 attached thereto. Mount points 68 have pivots 70 therein. Gantry 12 includes a non-rotating base 72 and a rotatable base 74 (shown in hidden lines). In operation, non-rotating base 72 and rotatable base 74 of gantry 12 may be pivoted about pivots 70 in order to control a tilt angle between an axis of rotation 76 of gantry 12 and the patient 22 of FIGS. 1 and 2.

Gantry 12 includes the non-rotating base 72, which houses bearings, electronics, cables, and support hardware (not shown) for the rotatable base 74. Rotatable base 74 typically includes, as illustrated in FIGS. 1 and 2, detector assembly 18 (which includes detectors 20 and DAS 32), x-ray source 14, a high voltage generator, and other equipment for operation of a CT imaging system as would be understood by those skilled in the art. Generally, the x-ray source 14 and the detector assembly 18 of FIGS. 1 and 2 are mounted to the rotatable base 74 and rotated about an imaging volume and about the subject.

Figure 6:
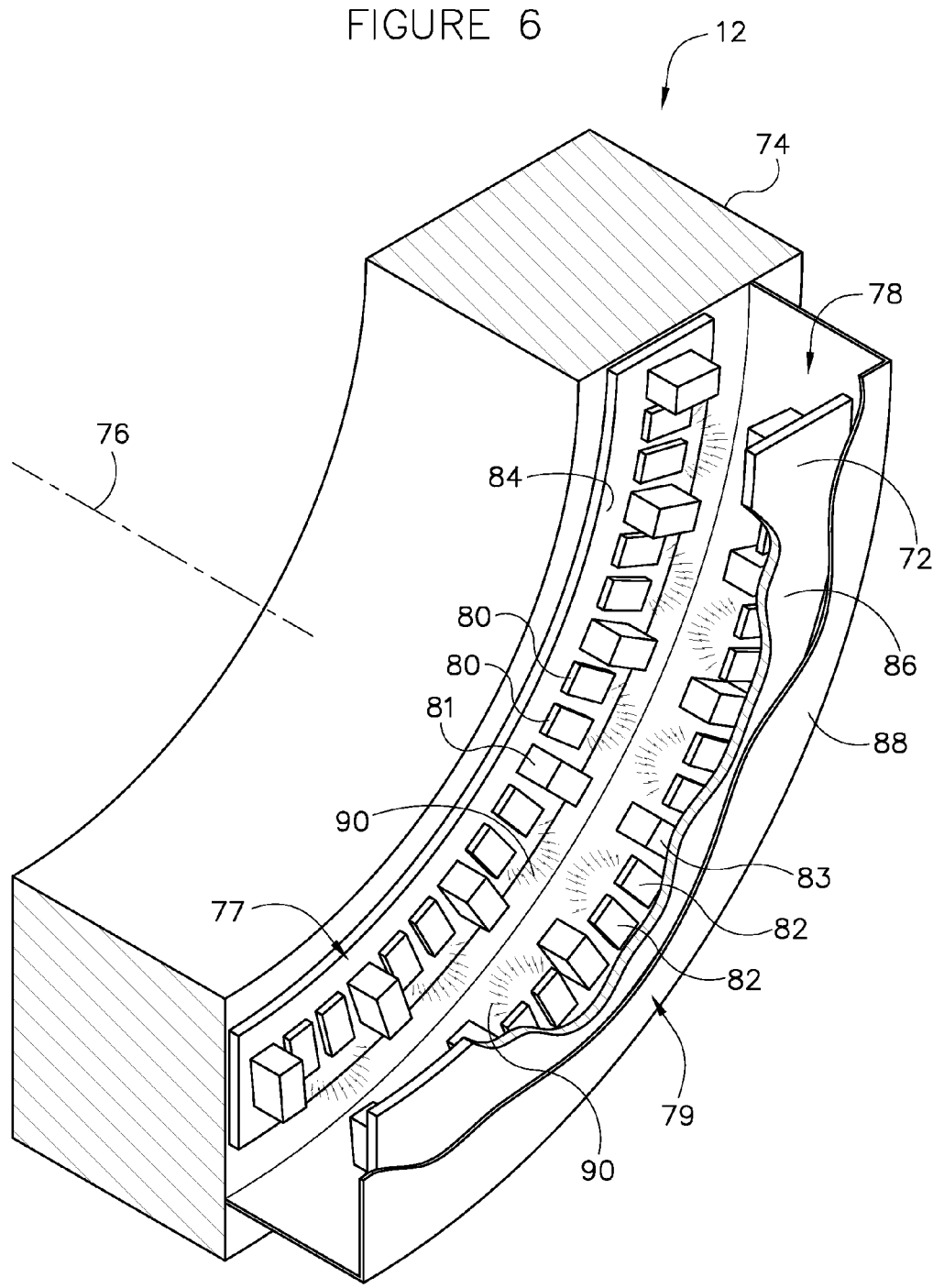
FIG. 6 is a perspective view of a CT gantry according to an embodiment of the present invention.

FIG. 6 illustrates a perspective section view of gantry 12 according to an embodiment of the present invention. A portion of stationary base 72 is illustrated that is in proximity to a portion of rotatable base 74. An optical communication system 78 includes a plurality of modules 77, 79. In an embodiment of the present invention, module 77 includes a plurality of light sources 80 and receivers 81 positioned on a mount base 84 attached to the rotatable base 74, and module 79 includes a plurality of light sources 82 and receivers 83 positioned on a mount base 86 attached to the stationary base 72. Mount bases 84, 86, in an example, may include printed wiring assemblies (PWAs) made of a circuit board substrate material, or may include flex circuits mounted on a substrate. Light sources 80, 82, in an embodiment of the present invention, include devices that emit light in the visible light spectrum, such as LEDs. In alternate embodiments, light sources 80, 82 may include devices that emit in the infrared or the ultraviolet spectrum. Furthermore, although modules 77, 79 illustrate two light sources 80, 82 for each light receiver 81, 83, one skilled in the art will recognize that there may be more, or fewer light sources 80, 82 per light receiver 81, 83. For instance, each module 77, 79 may instead include three light sources 80, 82 per receiver 81, 83.

Additionally, one skilled in the art will recognize that the arrangement of light sources 80, 82 and receivers 81, 83 may be altered from one another on the two modules 77, 79 to prevent "dead spots" therebetween. Accordingly, as module 77 passes module 79 during rotation of rotatable base 74, or while the rotatable base 74 is stationary, the two modules 77, 79 will have light sources 80, 82 emitting to receivers 81, 83 such that, for any orientation of the two modules 77, 79, no "dead zones" occur therebetween. In other words, modules 77, 79 may have sources 80, 82 and receivers 81, 83 arranged thereon in two modular designs such that there are not "dead-zones" where all of the receivers 81, 83 on one side are lined up with receivers 81, 83 on the other side.

Figure 7:
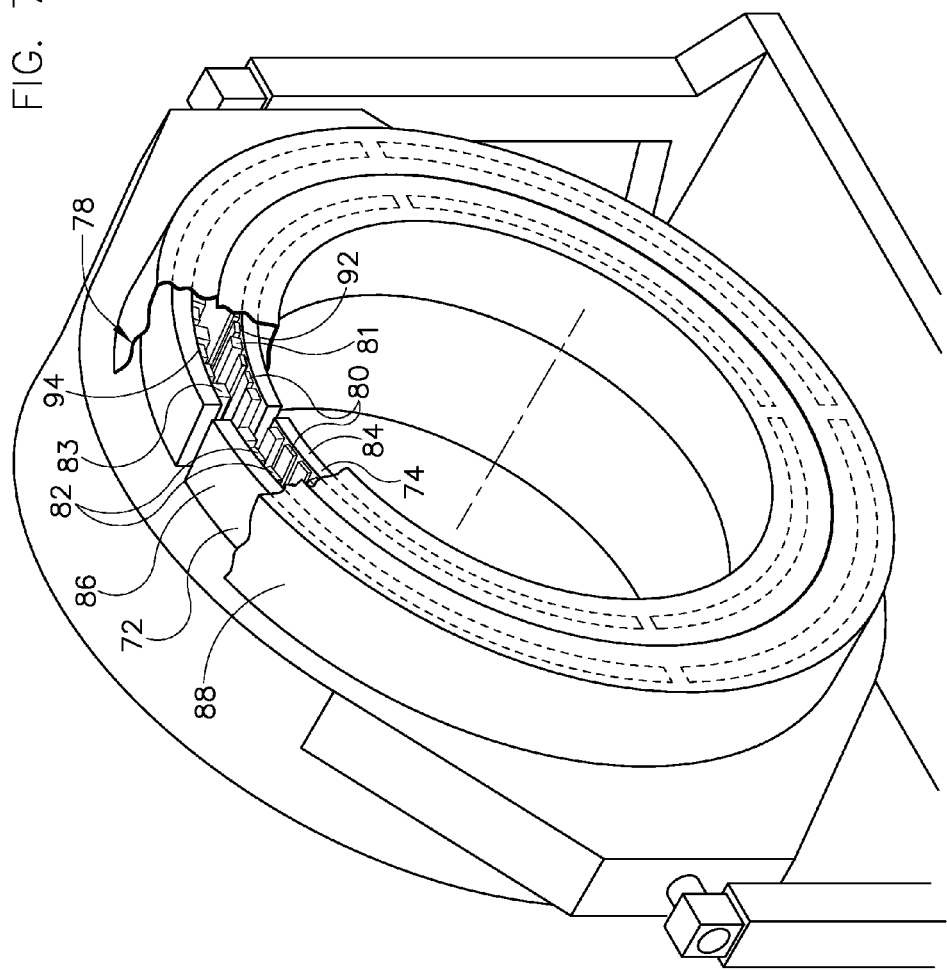
FIG. 7 is a perspective view of a CT gantry according to another embodiment of the present invention.

Still referring to FIG. 6, mount bases 84, 86 may be designed in a modular fashion. In other words, mount bases 84, 86 may each include an arrangement of light sources 80, 82 and receivers 81, 83 that is substantially the same, such that a single design of mount bases 84, 86 may be implemented for manufacturing efficiency, simplicity, and reduced cost. In this fashion, a single design of an arrangement of light sources 80, 82 and receivers 81, 83 may be fabricated for use on both the rotatable base 74 and the stationary base 72. The modular design, according to an embodiment of the present invention, may occupy, for instance, 90° of arc coverage of gantry 12 as illustrated in FIG. 7. Accordingly, in an exemplary embodiment, four modules 77, each having 90° of arc coverage, may be positioned about the arc of the rotatable base 74 to provide 360° of coverage. Likewise, four modules 79, each having 90° of arc coverage may be positioned about the circumference of the stationary base 72, in order to provide 360° of coverage. One skilled in the art will recognize that a modular arrangement of light sources and receivers 80-83 need not be limited to the 90° of arc coverage as illustrated in FIG. 7. Rather, one skilled in the art would recognize that a modular design may include coverage less than or greater than 90° per module, while providing a single modular design that will provide for instance 360° coverage by using multiple modules 77, 79 attached around the circumferences of the rotatable base 74 and stationary base 72.

According to an embodiment of the present invention, an optional shroud 88 encloses optical communication system 78 such that optical communication between light sources 80, 82 and light receivers 81, 83 may be protected from external light or other interfering signals generated from sources outside the optical communication system 78. Shroud 88 thus may provide light isolation and may not be necessary for the optical communications system 78 in order to meet, for instance, radiated and conducted emissions standards and immunity.

In operation, rotatable base 74 is caused to rotate about the axis of rotation 76 of gantry 12. As such, the mount base 84 is caused to rotate continuously past the mount base 86. Accordingly, digitized optical signals 90 generated by light sources 80 mounted on the rotatable base 74 may be received by light receivers 83 that are mounted on the stationary base 72. Likewise, digitized optical signals 91 generated by light sources 82 mounted on the stationary base 72 may be received by light receivers 81 that are mounted on the rotating base 74. As such, optical signals 90, 91 may pass between the rotatable base 74 and the stationary base 72 by use of light sources and receivers 80-83 of the optical communication system 78, thus providing a digital communication therebetween.

Because the shroud 88 protects, or isolates, the light receivers 81, 83 from external light sources, the optical communication system 78 provides contactless, low noise transfer of digital data between the rotating base 74 and the stationary base 72, and vice-versa. In embodiments of the present invention, an excess number of light sources and receivers 80-83 are provided in order to enable redundant coverage between the stationary base 72 and the rotating base 74. As such, the light sources and receivers 80-83 are caused to operate in parallel, and light emission between the rotating and stationary components is redundantly transmitted and received, thus ensuring robust communication therebetween. Operation may include parallel operation of sources 80 emitting to receivers 83. Operation may also include parallel operation of sources 82 emitting to receivers 81. Additionally, operation may also include simultaneous operation of sources 80 and sources 82, such that light emitted therefrom is received by respective receivers 83, 81, which may be accomplished by ensuring light emitting from a source on the same base as the receiver is not received at the receiver. In other words, for simultaneous operation of both sets of sources 80, 82, light emitting from sources 80 will emit to and be received by receivers 83, while not being received by receivers 81. Likewise, light emitting from sources 82 will emit to and be received by receivers 81, while not being received by receivers 83. In this fashion, simultaneous operation of sources 80, 82 may occur without causing interference in the receivers that reside on the same base as the sources. Additionally, operation may also include the use of a combination of transmission wavelengths, visible, infrared, or ultraviolet such that electromagnetic energy in one direction from 80 to 83 could be in one spectrum while communication from 82 to 81 would be in a differing spectrum, thus providing increased crosstalk immunity.

According to an embodiment of the present invention, the number of light sources 80, 82 may be greater than a number of light receivers 81, 83 in order to better ensure communication between the rotating and stationary components and in order to provide additional robustness. Accordingly, each of the light receivers 81, 83 may be configured in a manner that will allow error correction if one or more of the light receivers 81, 83 does not receive enough illumination.

Furthermore, according to yet another embodiment of the present invention, the light receivers 81, 83 and the mount bases 84, 86 may be designed as black bodies in order to reduce reflection within the optical communication system 78 such that light incident upon such components tends to be absorbed, and not reflected, thus improving the robustness of operation.

FIG. 7 illustrates an optical communication system 78 according to an alternate embodiment of the present invention. In this embodiment, mount bases 84, 86 having optical sources and receivers 80-83 mounted thereon, are positioned on circumferential surfaces 92, 94 of the rotating base 74 and stationary base 72, respectively. In other words, light sources and receivers 80, 81 may be mounted on an outer circumference surface 92 of the rotatable base 74, and light sources and receivers 82, 83 may be positioned on an inner circumference surface 94 of the stationary base 72. Shroud 88 is positioned therearound in order to optically isolate the optical communication system 78 from external sources.

As such, an embodiment of the present invention, as illustrated in FIG. 7, may operate in a fashion similar to that described regarding FIG. 6, wherein contactless optical communication is provided between a rotating base 74 and a stationary base 72, and vice versa. As such, in this embodiment, redundant and parallel information is transmitted and received, which may, likewise, provide an opportunity for error correction in the transmitted data.

Figure 8:
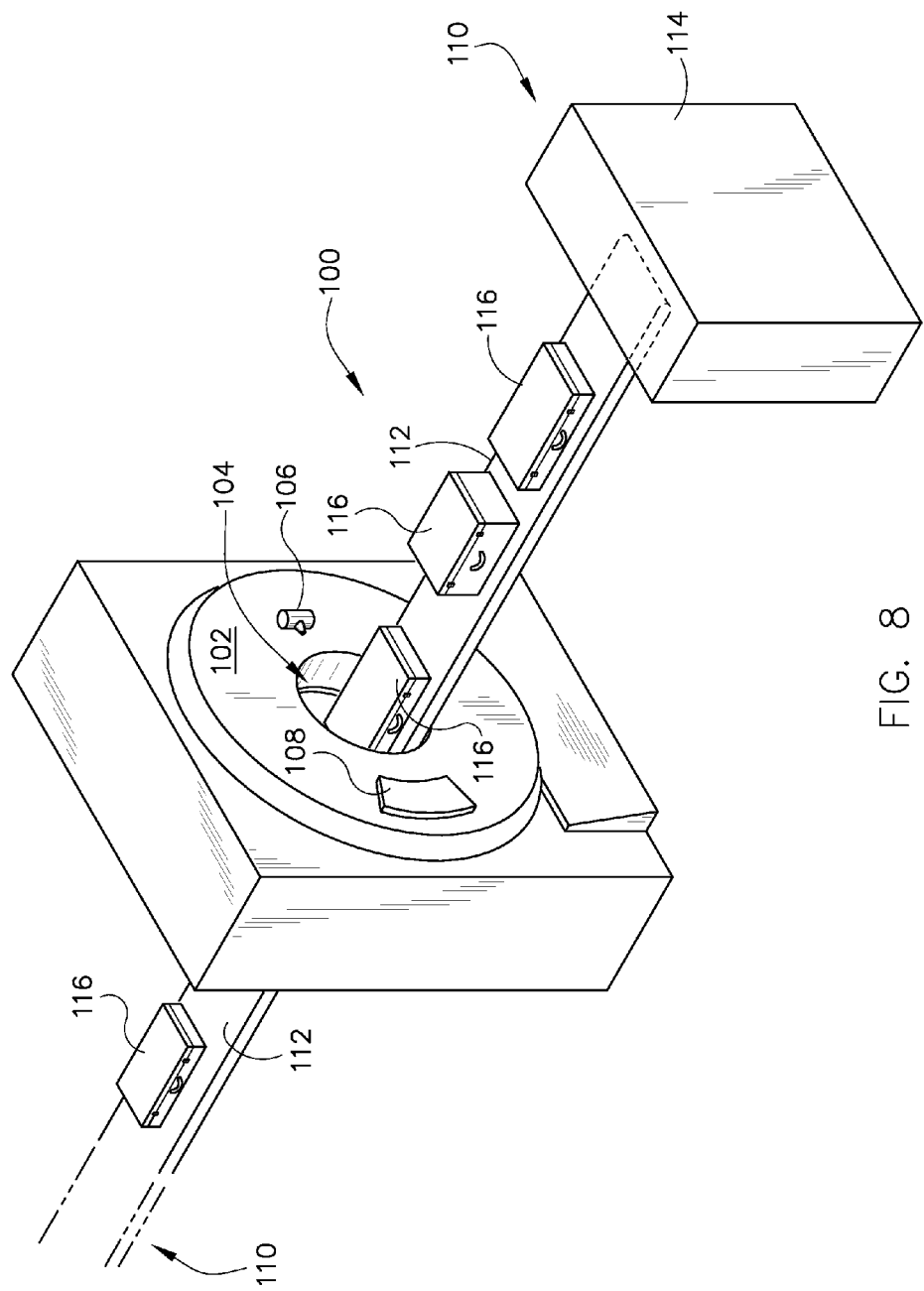
FIG. 8 is a pictorial view of a CT system for use with a non-invasive package inspection system.

Referring now to FIG. 8, package/baggage inspection system 100 includes a rotatable gantry 102 having an opening 104 therein through which packages or pieces of baggage may pass. The rotatable gantry 102 houses a high frequency electromagnetic energy source 106 according to an embodiment of the present invention, as well as a detector assembly 108 having scintillator arrays comprised of scintillator cells. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc. Additionally, such systems may be used in industrial applications for non-destructive evaluation of parts and assemblies.

According to one embodiment of the present invention, an optical communication system includes a rotatable base having a plurality of optical sources and optical receivers mounted thereon, and a stationary base having a plurality of optical sources and optical receivers mounted thereon. The system is configured to send and receive optical signals bi-directionally between the rotatable base and the stationary base.

In accordance with another embodiment of the present invention, a method of manufacturing a communication system between a rotating base and a stationary base includes attaching a first printed wire assembly (PWA) to a rotatable base, the first PWA having mounted thereon at least one light source and at least one light receiver, attaching a second PWA to a stationary base, the second PWA having mounted thereon at least one light source and at least one light receiver. The method further includes positioning the rotatable base and the stationary base proximate to one another, emitting light from one of the first and second PWAs, and receiving the light by the other of the first and second PWAs.

Yet another embodiment of the present invention includes a CT system includes a high frequency electromagnetic energy projection source configured to project a high frequency electromagnetic energy beam toward an object, a detector array having a plurality of scintillator cells wherein each cell is configured to detect high frequency electromagnetic energy passing through the object, and a data acquisition system (DAS) connected to the detector array and configured to receive outputs from detector array. The CT system further includes a rotatable gantry having an opening to receive the object to be scanned, the rotatable gantry having a rotatable base and a stationary base positioned proximate the rotatable base, a plurality of modules each having at least one light source and at least one light receiver positioned thereon, wherein at least one of the plurality of modules is mounted on the rotatable base, and wherein at least one of the plurality of modules is mounted on the stationary base, and a computer programmed to send and receive optical signals bi-directionally between the rotatable base and the stationary base while the rotatable base is rotating and while the rotatable base is stationary.

The present invention has been described in terms of the preferred embodiment, and it is recognized that equivalents, alternatives, and modifications, aside from those expressly stated, are possible and within the scope of the appending claims.

What is claimed is:

1. An optical communication system comprising:
   a rotatable base having a plurality of optical sources and optical receivers mounted thereon; and
   a stationary base having a plurality of optical sources and optical receivers mounted thereon;
   wherein the system is configured to send and receive optical signals bi-directionally between the rotatable base and the stationary base; and
   wherein the optical sources and optical receivers are mounted on at least one printed wiring assembly (PWA).

2. The optical communication system of claim 1 wherein the system is further configured to send and receive optical signals while the rotatable base is rotating and while the rotatable base is stationary.

3. The optical communication system of claim 1 wherein a subset of the optical sources and optical receivers of one of the rotatable base and the stationary base are arranged on a module having a single modular design.

4. The optical communication system of claim 1 wherein a subset of the optical sources and optical receivers of one of the rotatable base and the stationary base are arranged in two modular designs such that there are not "dead-zones" where all of the receivers on one side are lined up with receivers on the other side.

5. The optical communication system of claim 1 wherein at least two of the plurality of optical sources on one of the rotatable base and the stationary base emit an optical signal in parallel with one another.

6. The optical communication system of claim 1 wherein one of the rotatable base and stationary base are components of a CT gantry.

7. The optical communication system of claim 6 wherein the plurality of optical sources and optical receivers of the rotatable base are positioned on a planar face of the rotatable base, and the plurality of optical sources and receivers of the stationary base are positioned on a planar face of the stationary base, such that the planar faces oppose one another.

8. The optical communication system of claim 6 wherein the plurality of optical sources and optical receivers of the rotatable base are positioned along an outer circumference of the rotatable base and the plurality of optical sources and receivers of the stationary base are positioned along an inner circumference of the stationary base.

9. The optical communication system of claim 6 wherein the CT gantry is for one of a medical imaging system and a baggage imaging system.

10. The optical communication system of claim 1 wherein one of the optical sources of the plurality of optical sources is an LED.

11. The optical communication system of claim 1 wherein the number of optical sources of the plurality of optical sources on one of the rotatable base and the stationary base is greater than the number of optical receivers of the plurality of optical receivers.

12. The optical communication system of claim 1 wherein the optical signals are in one of the visible light, the infrared, and the ultraviolet spectrum, or a combination of these where communication in one direction is in one spectrum and the other direction is in a different spectrum.

13. The optical communication system of claim 12 further comprising a shroud positioned to intercept visible light emitting toward the plurality of optical receivers from light sources that are external to the optical communication system.

14. A method of manufacturing a communication system between a rotating base and a stationary base, the method comprising:
attaching a first printed wire assembly (PWA) to a rotatable base, the first PWA having mounted thereon at least one light source and at least one light receiver;
attaching a second PWA to a stationary base, the second PWA having mounted thereon at least one light source and at least one light receiver;
positioning the rotatable base and the stationary base proximate to one another;
emitting light from one of the first and second PWAs; and
receiving the light by the other of the first and second PWAs.

15. The method of manufacturing of claim 14 wherein the light emitted is in one of the visible light spectrum, the infrared light spectrum, and the ultraviolet light spectrum, or a combination thereof where communication in one direction is in one spectrum and the other direction is in a different spectrum.

16. The method of manufacturing of claim 14 further comprising emitting the light in parallel from at least two light sources of one of the first and second PWAs.

17. The method of manufacturing of claim 14 wherein one of the rotating base and the stationary base are part of a CT gantry.

18. The method of manufacturing of claim 14 wherein attaching the first PWA further comprises attaching the first PWA to a planar surface of the rotatable base, and wherein attaching the second PWA further comprises attaching the second PWA to a planar surface of the stationary base.

19. The method of manufacturing of claim 14 wherein attaching the first PWA further comprises attaching the first PWA to an outer circumferential surface of the rotatable base, and wherein attaching the second PWA further comprises attaching the second PWA to an inner circumferential surface of the stationary base.

20. A CT system comprising:
a high frequency electromagnetic energy projection source configured to project a high frequency electromagnetic energy beam toward an object;
a detector array having a plurality of scintillator cells wherein each cell is configured to detect high frequency electromagnetic energy passing through the object;
a data acquisition system (DAS) connected to the detector array and configured to receive outputs from detector array;
a rotatable gantry having an opening to receive the object to be scanned, the rotatable gantry having a rotatable base and a stationary base positioned proximate the rotatable base;
a first module coupled to the rotatable base, the first module comprising:
an emission source configured to emit a signal in a first spectrum; and
a receiver configured to receive a signal in a second spectrum that is different from the first spectrum;
a second module coupled to the stationary base, the second module comprising:
an emission source configured to emit a signal in the second spectrum; and
a receiver configured to receive a signal in the first spectrum; and
a computer programmed to send and receive the signals bi-directionally between the rotatable base and the stationary base while the rotatable base is rotating and while the rotatable base is stationary.

21. The CT system of claim 20 wherein the first and second spectra are selected from the group consisting of a visible light spectrum, an ultraviolet spectrum, and an infrared spectrum.

22. The CT system of claim 20 wherein the at least one of the plurality of modules mounted on the rotatable base is mounted on a planar face of the rotatable base, and wherein the at least one of the plurality of modules mounted on a stationary base is mounted on a planar face of the stationary base.

23. The CT system of claim 20 wherein the at least one of the plurality of modules mounted on the rotatable base is mounted on an outer circumference of the rotatable base, and wherein the at least one of the plurality of modules mounted on the stationary base is mounted on an inner circumference of the stationary base of the stationary base.

24. The CT system of claim 20 wherein the emission source and receiver of the first module are mounted on a first printed wiring assembly (PWA); and
wherein the emission source and receiver of the second module are mounted on a second PWA.

\* \* \* \* \*